(12) United States Patent
Hiramoto et al.

(10) Patent No.: US 6,798,503 B2
(45) Date of Patent: Sep. 28, 2004

(54) EDGE FLAW INSPECTION DEVICE

(75) Inventors: Kazuyuki Hiramoto, Tokyo (JP); Takashi Kanno, Koshigaya (JP)

(73) Assignee: Raytex Corporation (JP)

( * ) Notice: Subject to any disclaimer, the term of this patent is extended or adjusted under 35 U.S.C. 154(b) by 0 days.

(21) Appl. No.: 10/402,229

(22) Filed: Mar. 27, 2003

(65) Prior Publication Data

US 2003/0184743 A1 Oct. 2, 2003

(30) Foreign Application Priority Data

Mar. 28, 2002 (JP) .................................... P2002-091866

(51) Int. Cl.[7] .............................................. G01N 21/00
(52) U.S. Cl. ............................... 356/237.1; 356/237.5; 250/559.36
(58) Field of Search ..................... 356/237.1–237.5, 356/445, 446; 250/559.36

(56) References Cited

U.S. PATENT DOCUMENTS

| 4,095,905 A | 6/1978 | Kuni et al. ................. 356/200 |
| 4,597,665 A | 7/1986 | Galbraith et al. ............ 356/237 |
| 6,147,357 A | * 11/2000 | Nicolesco ............... 250/559.46 |
| 2002/0005946 A1 | 1/2002 | Oomori et al. .......... 356/237.2 |

FOREIGN PATENT DOCUMENTS

| EP | 3626724 A1 | 2/1988 | .......... G01B/11/30 |
| JP | 5-142036 | * 6/1993 | |
| JP | 8-86623 | 4/1996 | .......... G01B/11/24 |
| JP | 9-269298 | 10/1997 | |
| JP | 11-351850 | 12/1999 | |

* cited by examiner

Primary Examiner—Hoa Q. Pham
(74) Attorney, Agent, or Firm—Ostrolenk, Faber, Gerb & Soffen, LLP

(57) ABSTRACT

This device is provided with an elliptical mirror 2, a light source 5 that radiates coherent light towards an inspected edge 4 arranged near the location of its first focal point, a light blocking member 6 that blocks diffracted light of a low order that is radiated from light source 5 and reflected by inspected edge 4, and a photo detector arranged at the location of a second focal point 7 of the elliptical mirror 2. The light blocking member 6 is composed of a light absorbing member arranged on the mirrored surface of elliptical mirror 2 reached by the low order diffracted right.

6 Claims, 4 Drawing Sheets

EDGE FLAW INSPECTION DEVICE

BACKGROUND OF THE INVENTION

1. Field of the Invention

The present invention relates to an edge flaw inspection device that optically inspects flaws in inspected edges, and more particularly, to a device that detects flaws in components formed into the shape of plates such as silicon wafers and semiconductor wafers.

2. Background Art

Edge flaw inspection devices that detect edge flaws such as cracks, chips or polishing marks in long, narrow edges such as the outer edges of silicon wafers have a structure described in, for example, Japanese Patent No. 2999712 (Japanese Patent Application, First Publication No. Hei 9-269298).

As shown in FIG. 6, this edge flaw inspection device 20 is provided with an elliptical mirror 23 in the form of a concave mirror that is severed near the midpoint of a first focal point 21 and a second focal point 22, a light source 24 that radiates laser light towards first focal point 21 of elliptical mirror 23, a photo detector 25 arranged at second focal point 22, and a douser 26 arranged between first focal point 21 and light source 24. A slit 27 is formed along a horizontal plane that contains two focal points 21 and 22 (the direction of this plane is hereinafter to be the horizontal direction) in the apex of elliptical mirror 23. Reference symbol 30 in the drawing indicates a lens.

Slit 27 has a width that is slightly larger than the thickness of a silicon wafer 28, and a portion of silicon wafer 28 can be inserted within elliptical mirror 23 from outside elliptical mirror 23. Silicon wafer 28 that has been inserted into elliptical mirror 23 from slit 27 is held so that its outer peripheral edge does not pass first focal point 21. In addition, silicon wafer 28 is rotatably held about a vertical axis, and the outer peripheral edge arranged at first focal point 21 can be continuously changed in the peripheral direction.

Through hole 29 is formed in douser 26 on the light path that connects light source 24 and first focal point 21. Laser light emitted from light source 24 passes through through hole 29 of douser 26, and reaches the outer peripheral edge of silicon wafer 28 arranged at first focal point 21 where it is then reflected.

In the case of viewing silicon wafer 28 with its edge facing towards the front, there is a flaw in its edge as shown in FIG. 7, and if this flaw is a vertical flaw 31 that extends in the vertical direction, laser light radiated onto the edge is typically strongly scattered to the left and right. On the other hand, if a flaw that has occurred in the edge is a horizontal flaw 32, laser light radiated onto the edge is typically strongly scattered up and down.

This reflected light scattered at the peripheral edge of silicon wafer 28 at first focal point 21 is scattered three-dimensionally, reaches the mirrored surface of elliptical mirror 23, and is then reflected there after which it converges at second focal point 22. Since photo detector 25 is arranged at second focal point 22, the converted scattered and reflected light is detected by photo detector 25.

Since this scattered reflected light has different frequency components depending on the type of defect present in the peripheral edge of silicon wafer, its surface roughness and so forth, by detecting this light and analyzing its frequency components, the type of defect, surface roughness and so forth can be detected. In addition, as a result of rotating silicon wafer 28 about a vertical axis, its peripheral edge can be detected for flaws over its entire circumference.

On the other hand, light reflected from the surface other than the location of a flaw in the outer peripheral edge of silicon wafer 28 is in the form of low order diffracted light such as so-called regular reflected light. For example, regular reflected light from the outer peripheral edge of silicon wafer 28 arranged along the horizontal direction is predominantly light that is reflected in the vertical plane that contains first focal point 21 and second focal point 22 or its vicinity. However, since this low order diffracted light is light reflected by a surface other than that containing a flaw, and does not contain information necessary for detecting a flaw in the outer peripheral surface, it is preferable that it not be detected by photo detector 25.

In an edge flaw detection device 20 of the prior art, a douser 26 is provided in the form of a strip that extends in the vertical direction in the space between light source 24 and first focal point 21, which either prevents regular reflected light and other low order diffracted light from reaching the mirrored surface of elliptical mirror 23, or blocks low order diffracted light that has reached the mirrored surface of elliptical mirror 23 from reaching the second focal point after it has been reflected there.

However, in the case of a douser 26 arranged in the space between a light source and a first focal point as was previously described, the problem arises in which not only low order diffracted light such as regular reflected light, but also all diffracted light that attempts to pass through the space in which douser 26 is arranged ends up being blocked.

Namely, all diffracted light reflected by the outer peripheral edge of silicon wafer 28 is three-dimensionally scattered at first focal point 21, and proceeds through the plane that contains the scattering direction vector and the first and second focal points 21 and 22. However, in a device of the prior art in which douser 26 is arranged in the space between light source 24 and first focal point 21, even in the case of scattered diffracted light scattered by an edge flaw in the outer peripheral edge of silicon wafer 28, if the scattering direction vector is facing in a direction at an angle that is shallower than the vertical plane as in the manner of scattered diffracted light produced by a horizontal flaw, the plane through which the scattered diffracted light proceeds ends up intersecting with douser 26, thereby resulting in the problem of the scattered diffracted light being blocked by douser 26.

In this case, since diffracted light containing effective information relating to edge flaws cannot be detected by photo detector 25, there were cases in which it was difficult to judge the presence and types of defects.

In addition, as indicated in Japanese Unexamined Patent Application, First Publication No. 11-351850, although a method has been proposed in which regular reflected light is blocked and scattered diffracted light produced by a horizontal flaw is detected by arranging a light receiving element array in the vicinity of a first focal point, since the light receiving element array arranged in the space inside an elliptical mirror blocks scattered diffracted light effective for flaw detection, there was the problem of a decrease in the amount of information detected by a photo detector in the same manner as described above.

In consideration of the above circumstances, an object of the present invention is to provide an edge flaw inspection device that effectively eliminates low order diffracted light such as regular reflected light, but detects high order diffracted light such as scattered diffracted light in a photo detector without blocking that light.

SUMMARY OF THE INVENTION

An edge flaw inspection device of the present invention comprises: an elliptical mirror having a first focal point and a second focal points; a light source that radiates coherent light towards an inspected edge arranged near the first focal point of the elliptical mirror; a light blocking member that blocks diffracted light of a low order that is radiated from the light source and reflected by the inspected edge; and a photo detector arranged at the second focal point of the elliptical mirror; and the light blocking member comprising a light absorbing member arranged on the mirrored surface of the elliptical mirror reached by the low order diffracted right.

According to the present invention, coherent light emitted from a light source is reflected by an inspected edge. Since the inspected edge is arranged near a first focal point, the light is scattered three-dimensionally according to the status of the inspected edge. Since an elliptical mirror is arranged in the direction of scattering, light reflected by the mirrored surface of that elliptical mirror is diffracted towards the direction of a second focal point. Since a photo detector is provided at the second focal point, all of the reflected light converges at the second focal point where it is then detected.

In this case, although diffracted light of a low order that does not contain flaw information is present from the inspected edge, since the direction in which this low order diffracted light scatters is fixed to a certain extent, and a light blocking member composed of a light absorbing material is provided in the mirrored surface of the elliptical mirror arranged in the direction of scattering, low order diffracted light is absorbed by the light absorbing material, and is prevented from being detected by the photo detector. On the other hand, although other diffracted light is reflected by the mirrored surface of the elliptical mirror, since the light blocking member is only arranged on the mirrored surface, and is not arranged in the space inside the elliptical mirror as in the prior art, all scattered refracted light reflected by the mirrored surface of the elliptical mirror converges at the second focal point and is detected by the photo detector.

The light absorbing member may have a width corresponding to the distance from the first focal point. According to this aspect, although light reflected at the first focal point is reflected three-dimensionally in all directions, regular reflected light and other low order diffracted light that does not contain flaw information is also scattered over a prescribed angle range. Namely, light reflected over a prescribed angle range at the first focal point has a narrow width in the vicinity of the first focal point, that width increases the greater the distance from the first focal point. Thus, by making the width of the light absorbing material narrow close to the first focal point, and then increasing the width as the distance from the first focal point increases, low order diffracted light not required for detecting edge flaws is effectively absorbed, while high order diffracted light required for flaw detection can be effectively oriented towards the second focal point. The width of each part of the light absorbing member may be adjusted proportional to the distance from the first focal point to the each part.

The light absorbing member may be a masking tape composed from a light absorbing material. According to this invention, an edge flaw inspection device can be composed extremely easily by using masking tape for the light absorbing material. In addition, as a result of using masking tape, the light absorbing material can be easily attached to and removed from the elliptical mirror, and by adjusting the width of the masking tape, a device can be provided that can be matched to the type of edge flaw desired to be detected.

The inspected edge may be the periphery of a disk-shaped inspection target, and a focusing member is provided that forms an irradiated spot of coherent light formed at the inspected edge in a shape that is shorter in the peripheral direction than the thickness direction of the inspection target. According to this aspect, by inspecting a disk-shaped inspection target over a wide range in the direction of thickness, and narrowly focusing laser light in the peripheral direction, fine edge flaws can be effectively detected.

The focusing member may be one of a cylindrical lens, a rod lens, or a toric lens having a different radius of curvature in two directions.

DESCRIPTION OF THE PREFERRED EMBODIMENTS

Figure 1:
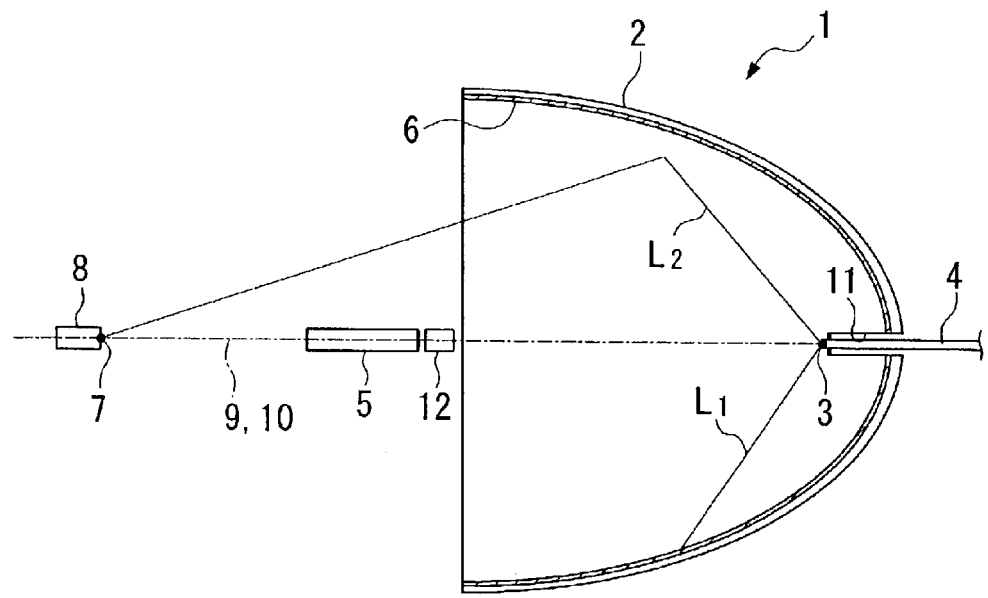
FIG. 1 is a cross-sectional view showing an edge flaw inspection device according to a first embodiment of the present invention severed along its vertical plane.
Figure 2:
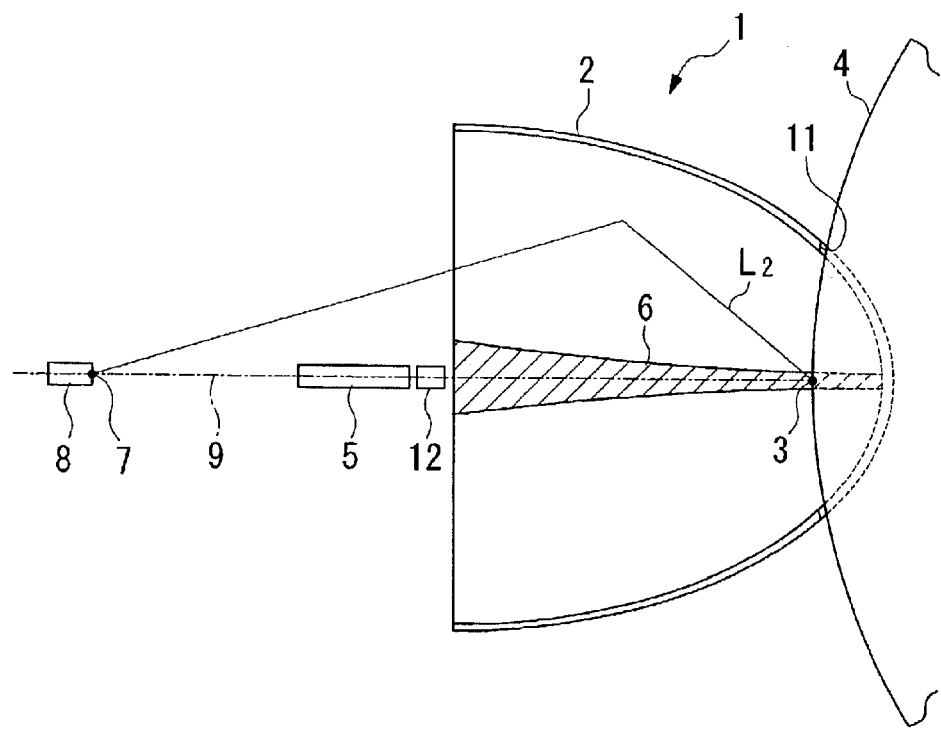
FIG. 2 is a cross-sectional view showing the edge flaw inspection device of FIG. 1 severed along its horizontal plane.
Figure 3:
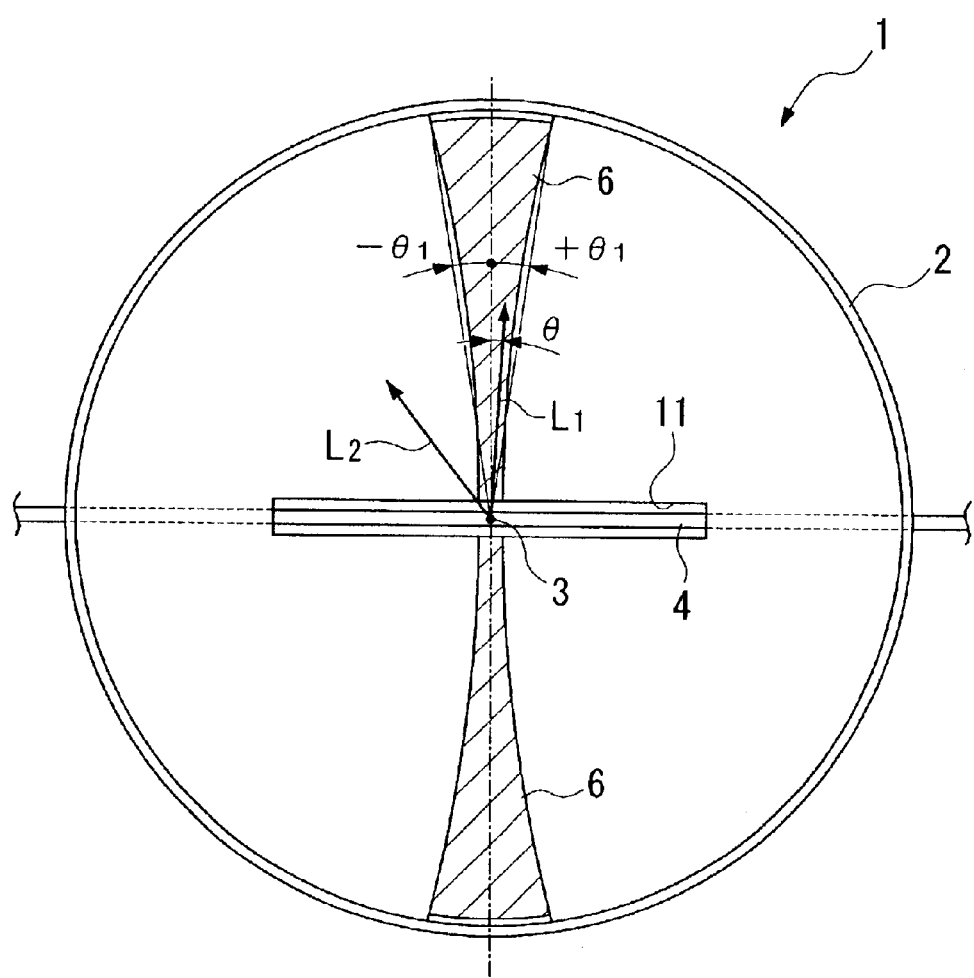
FIG. 3 is a front view of the edge flaw inspection device of FIG. 1 as viewed from the light source side.

The following provides an explanation of an edge flaw inspection device as claimed in a first embodiment of the present invention with reference to FIGS. 1 through 3.

An edge flaw inspection device 1 of the present embodiment is provided with an elliptical mirror 2, a light source 5 that radiates coherent light towards an edge (inspected edge) of a wafer 4 arranged near the location of a first focal point 3 of the elliptical mirror 2, a light blocking member 6 that blocks low order refracted light radiated from light source 5 that has been reflected by the edge of wafer 4, and a photo detector 8 arranged at the location of a second focal point 7 of elliptical mirror 2.

Elliptical mirror 2 is formed into roughly the shape of a semi-elliptical sphere severed at the plane that intersects a center line 9 that connects first focal point 3 and second focal point 7, and passes through nearly the midpoint of first focal point 3 and second focal point 7. In addition, the apex of elliptical mirror 2 is provided with a slit 11 cut along a horizontal plane 10 that contains the center line 9. This slit 11 is formed so as to allow insertion of a wafer 4 supported so as to be able to rotate horizontally outside elliptical mirror 2. Wafer 4 that has been inserted into slit 11 is moved by a positioning mechanism not shown to a location where its edge passes through first focal point 3 of elliptical mirror 2.

Light source 5 is, for example, a laser light source that is made to emit laser light (coherent light) towards first focal point 3 along center line 9 that connects first focal point 3 and second focal point 7. In the drawings, reference symbol 12 indicates a lens that causes the laser light to converge.

In consideration of deviation of the edge of wafer 4, it is necessary for the laser light to be slightly greater than the thickness of wafer 4, namely the diameter of the laser light beam must be larger than the thickness of about 600–800 μm of wafer 4.

On the other hand, the size of edge flaws attempted to be detected may be 50 μm or less. Thus, in order to adequately obtain scattered reflected light from microscopic edge flaws, it is necessary to focus the laser light to a beam diameter that is roughly the same size as the edge flaws. For example, in the case of radiating laser light having a beam diameter of 1000 μm for an edge flaw of 100 μm, the intensity of the scattered reflected light ends up decreasing. Thus, it is necessary to radiate laser light having a beam diameter of about 100 μm for edge flaws of 100 μm.

Figure 5:
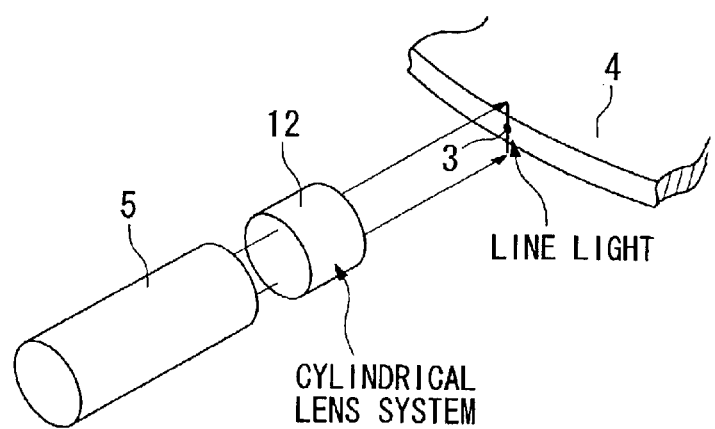
FIG. 5 is a perspective view showing a lens arranged between a light source and a first focal point.
Figure 6:
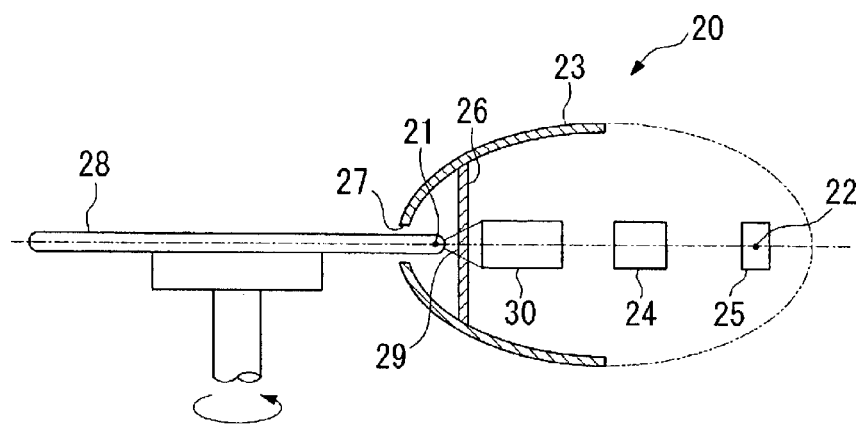
FIG. 6 is a vertical cross-sectional view showing an edge flaw inspection device of the prior art.
Figure 7:
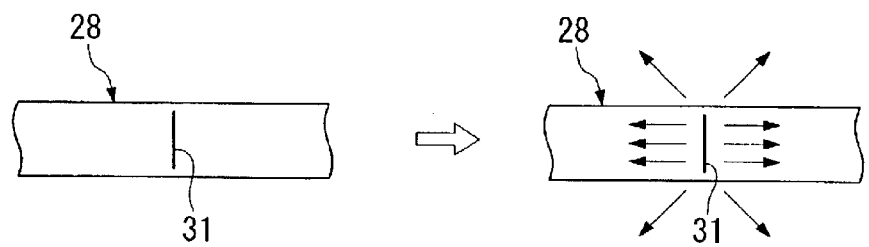
FIG. 7 is a front view showing a vertical flaw on the edge of a wafer and the status of the reflected light.
Figure 8:
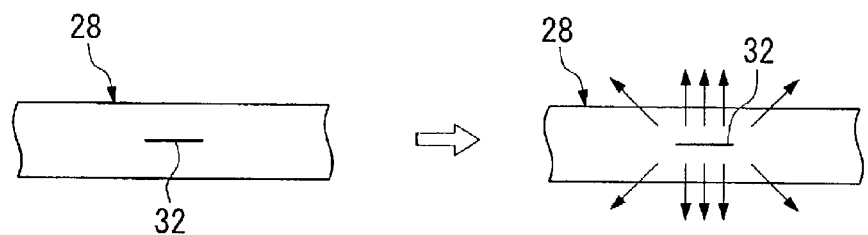
FIG. 8 is a front view showing a horizontal flaw on the edge of a wafer and the status of the reflected light.

In order to satisfy these mutually contradictory requirements, the laser light emitted from laser light source 5 is adjusted to be longer in the direction of thickness of wafer 4 and shorter in the peripheral direction. In order to accomplish this, as shown in FIG. 5, a cylindrical lens is used for lens (focusing member) 12 between laser light source 5 and first focal point 3. Furthermore, this lens 12 is not restricted to a cylindrical lens, but rather a rod lens or toric lens having a different radius of curvature in two directions may also be used.

Light blocking member 6 may be, for example, masking tape. Masking tape 6 has a surface composed of, for example, a black flocked material or other light absorbing material, and is composed to as to cover a portion of elliptical mirror 2 by affixing a adhesive surface on its back side to the mirrored surface of elliptical mirror 2. The location where masking tape 6 is affixed is the area to the left and right of a line that intersects with a vertical plane that contains center line 9 which connects first focal point 3 and second focal point 7.

In addition, as shown in FIGS. 2 and 3, the area where masking tape 6 that composes this light blocking member 6 is affixed is provided with a width that is proportional to the distance from first focal point 3. Namely, the width of masking tape 6 in the horizontal direction near the apex of elliptical mirror 2 arranged at a close distance from first focal point 3 is narrow, and this width increases as the distance from first focal point 3 increases.

The photo detector 8 is, for example, a photo diode.

The following provides an explanation of the operation of edge flaw inspection device 1 of the present embodiment composed in this manner.

According to edge flaw inspection device 1 of the present embodiment, when laser light emitted from light source 5 reaches first focal point 3 of elliptical mirror 2, it is reflected by the edge of wafer 4 arranged at first focal point 3. All of the light reflected by the edge of wafer 4 spreads out three-dimensionally from first focal point 3 serving as the origin, and is reflected in the direction of second focal point 7 after contacting the mirrored surface of elliptical mirror 2 arranged ahead.

In this case, since masking tape 6 is affixed to the mirrored surface of elliptical mirror 2 arranged near a vertical plane that contains first focal point 3 and second focal point 7, light reflected within the range of this masking tape 6 is absorbed by making tape 6 without reaching the mirrored surface of elliptical mirror 2.

Namely, light $L_1$ reflected by the edge of wafer 4 that forms a shallow angle θ with respect to the vertical plane that contains first focal point 3 and second focal point 7 is regular reflected light and other low order diffracted light, and consists mainly of light that does not have information required for detecting flaws in the edge of wafer 4. Thus, by absorbing this low order diffracted light with masking tape 6, light $L_1$ not required for flaw detection is removed, making it possible to effectively extract useful information.

In this case, in the edge flaw inspection device of the present embodiment, since the width of masking tape 6 changes in proportion to the distance from first focal point 3, although light $L_1$ reflected within the narrow angle range of $-\theta_1 \leq \theta \leq +\theta_1$ with respect to vertical plane P containing first focal point 3 and second focal point 7 is effectively removed, light $L_2$ outside that range that has information required for detecting flaws in the edge of wafer 4 can be prevented from being removed by masking tape 6.

Namely, light $L_1$ and $L_2$, for example, reflected at a fixed angle θ with respect to the vertical plane move away from vertical plane P as they move away from first focal point 3. Thus, as a result of the width of masking tape 6 being set to be narrow at locations near the first focal point, and the width of masking tape 6 being set to be wide at locations far from the first focal point, low order diffracted light $L_1$ reflected within the prescribed angle range of $-\theta_1 \leq \theta \leq +\theta_1$ with respect to vertical plane P can be effectively removed. In addition, light $L_2$ reflected outside this angle range $-\theta_1 \leq \theta \leq +\theta_1$ can be oriented towards second focal point 7 by being reflected by the surface of elliptical mirror 2 without being absorbed by masking tape 6.

In addition, according to edge flaw inspection device 1 of the present embodiment, since a structure is employed in which the mirrored surface of elliptical mirror 2 is masked, which differs from a structure in which a douser is arranged in the space inside elliptical mirror 2 as in the prior art, obstacles can be eliminated from the space inside elliptical mirror 2, and the blocking of light containing information effective for flaw detection from reaching second focal point 7 can be prevented. In addition, the use of masking tape 6 makes processing easier and is also convenient in terms of making it easy to reaffix the masking tape on the mirrored surface of elliptical mirror 2.

Moreover, according to edge flaw inspection device 1 of the present embodiment, by arranging cylindrical lens 12 between laser light source 5 and first focal point 3, the cross-section of the laser light can be formed to be long in the vertical direction, thereby making it possible to inspect edge flaws over the entire length in the direction of thickness of wafer 4. In addition, by focusing the laser light to be narrow in the peripheral direction of wafer 4, even fine edge flaws can be detected effectively.

Diffracted light 7 that has been converged at second focal point 7 in this manner is then detected by photo detector 8 arranged at second focal point 7. Since the detected diffracted light differs in intensity and frequency components depending on the types of defects formed in the edge of wafer 4, surface roughness and so forth, the intensity of the diffracted light, frequency components and so forth can be determined for each type of defect, and by then classifying the detected diffracted light, cracks, chips and flaws, etc. can be screened, and surface roughness can also be detected. In addition, by rotating wafer 4 horizontally about a vertical axis, flaws can be detected over its entire circumference.

Furthermore, in this edge flaw inspection device of the present embodiment, although the explanation has used the example of a disc-shaped wafer 4 for the inspection target, the inspection target is not restricted to this, but rather a wire-shaped member such as bonding wire and so forth can also be used for the inspection target besides the above plate-shaped target.

Figure 4:
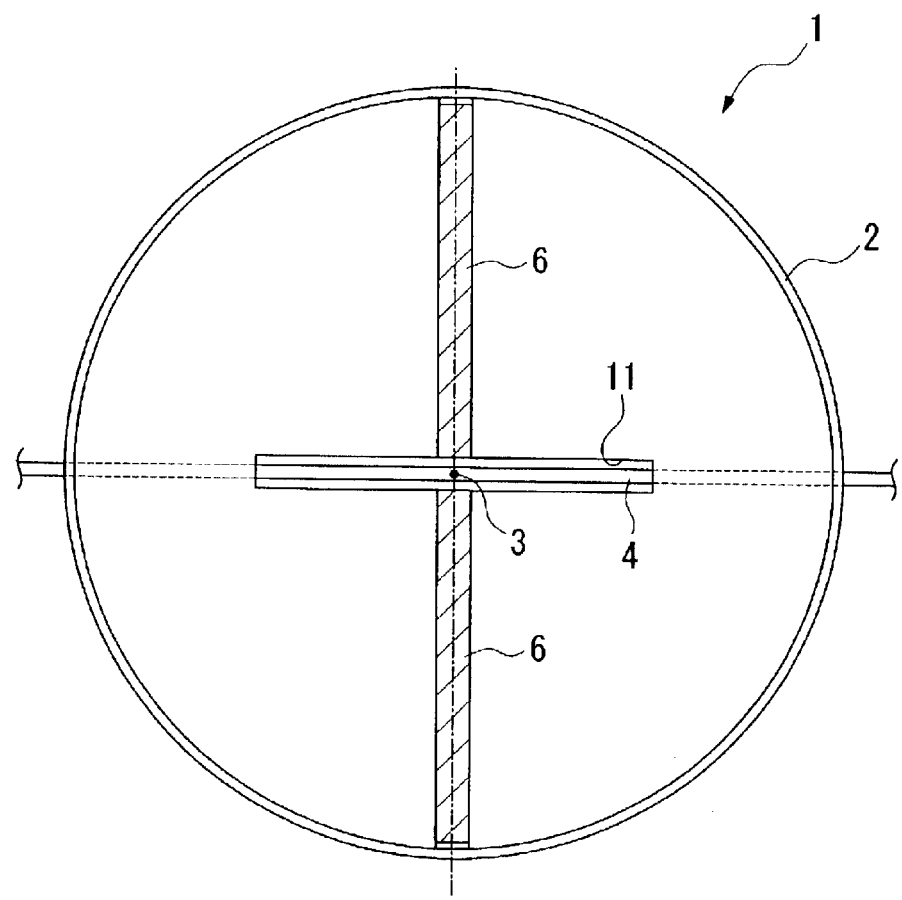
FIG. 4 is a front view showing a variation of the edge flaw inspection device of FIG. 1.

In addition, the dimensions and shape of elliptical mirror 2 as well as the width and other dimensions of masking tape 6 can be arbitrarily selected according to the type and properties of the inspection target. In the above embodiment in particular, although the width of the masking tape was changed corresponding to the distance from first focal point 3, instead of this, even if masking tape 6 is used that has a constant width irrespective of the distance from first focal point 3 as shown in FIG. 4, there is still the advantage of not having to form an obstacle in the space within elliptical mirror 2.

Moreover, instead of using masking tape affixed to the mirrored surface of elliptical mirror 2 for light blocking member 6, a light absorbing paint may be coated onto the mirrored surface of elliptical mirror 2, or a structure may be employed in which the elliptical mirror is removed from the relevant section.

In addition, although laser light radiated onto the edge of the inspection target was made to radiate along a center line that connects first focal point 3 and second focal point 7 of elliptical mirror 2, instead of this, the center line in the direction of the long axis of elliptical mirror 2 may be shifted slightly (by about 4°) relative to the optical axis of light source 5 so that light source 5 and the photo detector of detector 8 arranged at second focal point 7 do not overlap.

In this case, although the optical axis of light source 5 may be inclined in the horizontal direction relative to the center line in the direction of the long axis of elliptical mirror 2, it is preferably inclined in the vertical direction. This is because, if the laser light is radiated from a direction inclined in the horizontal direction from the center line in the direction of the long axis of elliptical mirror 2 relative to the edge of wafer 4 supported horizontally, reflected light scattered to the left and right that contains a large amount of information required for flaw detection ends up being biased to the left and right, thereby resulting in the problem of effective information being lost. On the other hand, if the light is inclined in the vertical direction, since reflected light scattered in the vertical direction does not contain a large amount of information required for flaw detection, the above problem is minimized.

Furthermore, even in the case of light being inclined in the horizontal direction, reflected light scattered to the left and right may be made to converge at the photo detector by making contrivances such as making the shape of elliptical mirror 2 laterally asymmetrical.

As has been explained above, according to the edge flaw inspection device as claimed in the present invention, since obstacles of scattered diffracted light can be eliminated from the space inside an elliptical mirror by arranging only a light blocking member on the mirrored surface of the elliptical mirror, all scattered diffracted light reflected by the mirrored surface can be converged at a second focal point, thereby making it possible to efficiently detect scattered diffracted light containing information required for flaw detection, and offering the advantage of being able to improve the accuracy of flaw detection.

What is claimed is:

1. An edge flaw inspection device comprising:

an elliptical mirror having a first focal point and a second focal points;

a light source that radiates coherent light towards an inspected edge arranged near the first focal point of the elliptical mirror;

a light blocking member that blocks diffracted light of a low order that is radiated from the light source and reflected by the inspected edge; and a photo detector arranged at the second focal point of the elliptical mirror; and the light blocking member comprising a light absorbing member arranged on the mirrored surface of the elliptical mirror reached by the low order diffracted light.

2. The edge flaw inspection device according to claim 1, wherein the light absorbing member has a width corresponding to the distance from the first focal point.

3. The edge flaw inspection device according to claim 1, wherein the light absorbing member is a masking tape composed from a light absorbing material.

4. The edge flaw inspection device according to claim 1, wherein the inspected edge is the periphery of a disk-shaped inspection target, and a focusing member is provided that forms an irradiated spot of coherent light formed at the inspected edge in a shape that is shorter in the peripheral direction than the thickness direction of the inspection target.

5. The edge flaw inspection device according to claim 4, wherein the focusing member is one of a cylindrical lens, a rod lens, or a toric lens having a different radius of curvature in two directions.

6. The edge flaw inspection device according to claim 1, wherein the width of each part of the light absorbing member is adjusted proportional to the distance from the first focal point to the each part.

* * * * *